United States Patent [19]

Shulman

[11] 3,943,248

[45] Mar. 9, 1976

[54] METHODS OF TREATING BURNS USING COLOPHONY CONTAINING PREPARATIONS

[76] Inventor: Max J. Shulman, 3209 S. Ocean Drive, Apt. 4L, Hallandale, Fla. 33009

[22] Filed: Nov. 4, 1974

[21] Appl. No.: 520,737

[52] U.S. Cl. .............. 424/196; 424/107; 424/238; 424/312; 424/DIG. 13
[51] Int. Cl.² ........................................ A61K 35/78
[58] Field of Search .......... 424/196, 195, 238, 317, 424/284, DIG. 13

[56] References Cited
UNITED STATES PATENTS
256,847   4/1882   Mayer............................ 424/196 X OTHER PUBLICATIONS
Merck Index 8th Ed., 1968 p. 923.
Chemical Abstracts 55:16707b (1961).
Chemical Abstracts 74:139372u (1971).
Hall, "Burn & Sunburn Remedies" Handbook of Non-Prescription Drugs, pp. 143–147 (1973).

Primary Examiner—Leonard Schenkman
Attorney, Agent, or Firm—Depaoli & O'Brien

[57] ABSTRACT

This invention relates to chemotherapeutic compositions and methods for topically treating traumatic, diseased and degenerative skin disorders.

One of the invention compositions comprises abietic acid and α-tocopherol contained in a pharmaceutically acceptable carrier. One or more of the invention compositions are suitable for the alleviation of severe burn injuries, and in the treatment of other skin disorders such as diabetic ulcers, decubitus ulcers, gangrene, abrasions, lacerations, puncture wounds, localized infections, and the like.

6 Claims, No Drawings

METHODS OF TREATING BURNS USING COLOPHONY CONTAINING PREPARATIONS

BACKGROUND OF THE INVENTION

The science of medicine has achieved dramatic progress in the last several decades. Certain pathological phenomena of the human constitution have resisted the advances of medical science. Diabetic and arteriosclerotic gangrene still constitute a disproportionate number of cases requiring surgical intervention. Even more serious, is the constant factor of several hundred thousand patients being treated for injury resulting from thermal, chemical and electrical burns. In the United States alone, as many as 14,000 persons die from trauma caused by burns every year.

The satisfactory treatment of burns remains unresolved. There is no consensus by the medical profession as to the superiority of any one particular burn treatment.

More recently there have been developed burn treatment techniques which have certain advantages over prior methods, but these techniques have been found to have serious disadvantages. Thus, the escharotic agents such as tannic acid and silver nitrate find limited usage because of their tendency to cause infection under the eschar and to result in scarring and contracture deformaties.

An old burn treatment method still in use is the application of protective coatings of petrolatum with padded pressure dressings. Another technique is the so-called "exposed" treatment involving the use of doses of morphine to control pain and the administration of intravenous plasma.

Of persons suffering trauma, none pose greater medical problems than burn patients. One of the pioneers of burn therapy has stated that "the mortality rate from a really large burn hasn't improved in the last thousand years. Our improvements in burn therapy are strictly limited to those that affect between 20 and 60 percent of the body surface. Above that, well, if a patient lives it's luck, not medicine, that's saved him."

Accordingly, it is a main object of the present invention to provide medicaments and methods for the treatment of persons suffering from severe burn injuries.

It is another object of this invention to provide chemotherapeutic compositions for the treatment of burn trauma covering more than 60% of a body surface, and to achieve survival of patients suffering from such severe burn trauma.

It is another object of this invention to provide pharmaceutical preparations especially adapted for the treatment of diabetic, arteriosclerotic, decubitus, varicose, and other pathogenic ulcers.

It is still another object of this invention to provide therapeutic preparations for application as a matrix in plastic and reconstructive surgery, involving epidermis, dermis and underlying tissue including cartilage, tendons and bones, and blood vessels.

It is a further object of the present invention to provide pharmaceutical compositions for the treatment of infections of the skin and underlying tissues, external ear infections and internal otitis media infections, and for prevention of infection following trauma, such as abrasions, lacerations and puncture wounds of the skin surface.

Other objects and advantages shall become apparent from the accompanying description and invention theory and practice.

DESCRIPTION OF THE INVENTION

The present invention vascular chemotherapeutic compositions and methods of treating skin injuries and disorders relate to experimental and clinical data derived from innovative approaches to the treatment and cure of topical injuries and disorders encountered by a physician in a career of medical practice.

One or more objects of the present invention are achieved by the provision of a chemotherapeutic composition comprising abietic acid, $\alpha$-tocopherol and a pharmaceutically acceptable vehicle, solvent or diluent.

The term "abietic acid" is meant to include diterpene resin acids of the formula $C_{19}H_{29}COOH$, and their anhydrides, which constitute the chief constituents of gum oleoresin from Pinus palustris and other conifers. Colophony (i.e., rosin) consists of about 90% resin acids and 10% neutral matter. Of the resin acids about 90% are isomeric with abietic acid; the other 10% is a mixture of dihydroabietic acid ($C_{20}H_{32}O_2$) and dehydroabietic acid ($C_{20}H_{28}O_2$). Neoabietic acid is a primary isomeric form of abietic acid.

For the purposes of the present invention the abietic acid component of the invention compositions can be employed directly in the form of colophony as it is produced and sold as naval stores. If desired, the resin acids of colophony can be separated from the inert matter and other non-therapeutic components by extraction of the resin acids with alkali, or by other methods. The separation and purification of abietic acid and resin acids of colophony are described in chapter II of "Natural Products Related to Phenanthrene," 3rd edition (Fieser and Fieser, Reinhold, New York, 1949).

$\alpha$-Tocopherol is naturally derived Vitamin E found mainly in plant materials. Some of the richest sources are seed germ oils, alfalfa, and lettuce. $\alpha$-Tocopherol found in nature is usually accompanied by two other active factors, $\beta$-tocopherol and $\gamma$-tocopherol.

Illustrative of suitable pharmaceutically acceptable carriers, solvents or diluents are vegetable oils such as olive oil, linseed oil, cottonseed oil, and the like; fish oil such as cod liver oil; and other readily available media such as mineral oil; sesame oil; silicone oil; lanolin; petrolatum; beeswax; unguentum; polyoxyalkylene glycols; carbowaxes; glyceryl monolaurate, polyoxyalkylene sorbitols; stearoyl diacetin; and the like. The invention compositions can be in the form of solutions, emulsions, suspensions, creams, salves, ointments and other similarly convenient forms for ease of topical application and therapeutic effectiveness. Non-aqueous media are preferred. Abietic acid and $\alpha$-tocopherol dissolved in olive oil is a particularly preferred chemotherapeutic composition of the present invention for the topical treatment of traumatic and degenerative disorders of the skin.

The abietic acid component is incorporated in the invention compositions in a quantity between about 15 and 90 percent based on the total weight of the composition. The amount of abietic acid employed is largely determined by the therapeutic application for which it is intended. On the average the quantity of abietic acid in the compositions will vary between about 25 and 60 percent of the composition weight.

α-Tocopherol is incorporated in the invention compositions in a quantity between about 2 and 40 percent based on the weight of abietic acid in the compositions.

The invention chemotherapeutic compositions are readily prepared by simple admixing of the composition ingredients. For example, abietic acid and α-tocopherol readily dissolve in olive oil with gentle warming to form a clear solution.

INVENTION THEORY AND PRACTICE

The present invention chemotherapeutic compositions which are adapted for specialized application in the treatment of pathological skin conditions, find antecedence in certain surprising and unexpected clinical manifestations observed in controlled medical experimentation.

It had been known and recorded in the early history of medical practice that natural products such as oleoresins appeared to have some beneficial effects when applied to a variety of human ailments. Ancient remedies in the form of liniments, salves, poultices and tonics often had contained an ingredient such as turpentine, balsam tar, pine tar, rosin, gum resins, and the like. Because such ingredients tended to irritate the skin, the ingredient was employed in small quantities and in a highly diluted state.

The early U.S. patent literature reports a number of preparations containing oleoresins which are recommended for relief of all manner of human ailments. Some of the preparations include upwards of ten to twenty ingredients.

U.S. Pat. No. 75,732 describes a liniment containing terpentine and pine tar, and recommends its use for reducing skin inflammation. U.S. Pat. No. 238,507 describes a liniment containing terpentine and pine tar for treatment of all types of skin injury including burns. The ointment of U.S. Pat. No. 247,479 contains terpentine and rosin, and is intended for the cure of scab in sheep. The salve of U.S. Pat. No. 256,847 for skin diseases contains rosin as one ingredient. The poultice of U.S. Pat. No. 308,243 contains pine tar and is recommended for felons, carbuncles and abscesses. U.S. Pat. No. 1,426,002 describes a salve containing rosin for skin treatment, and U.S. Pat. No. 2,361,756 proposes a pine tar ointment for general use in skin disorders.

The present invention in the early stages of development involved a program of testing a select group of natural gums and resins as therapeutic agents. It was discovered that concentrated solutions of colophony when applied to traumas of the skin and underlying tissue, rather than irritate and exacerbate the wound area, the solution promoted rapid healing without development of scar tissue.

The study of the dermatological application of concentrated colophony solutions was extended to include treatment of a broad variety of traumatic and degenerative skin disorders. There was consistent evidence that colophony (i.e., abietic acid derivatives), can act as an unusually effective therapeutic agent in the treatment of skin injuries. Burns, ulcers, infections, abrasions and wounds were treated with concentrated solutions of colophony.

The first clinical tests with colophony preparations were with minor infections such as onychia and paronychia of finger extremities. The results were favorable, and this encouraged further testing.

Concentrations of 25–35 weight percent of colophony in olive oil were applied as a treatment of lymphangitis-cellulitis, small and large abscesses, carbuncles, adenitis of the inguinal and auxillary lymph glands, phlebitis, and a variety of ulcers including varicose, traumatic, indolent, arteriosclerotic, decubitus and diabetic ulcers. A 15 weight percent colophony in olive oil terminated pain and infection in the otitis media without mastoid involvement.

An adult female had an axillary abscess incised and drained and received penicillin parenterally. After 2 weeks, the abscess recurred and it was incised and drained and the patient was prescribed oral antibiotics. When the abscess condition persisted, a 25 weight percent colophony ointment preparation was applied to the infected area, and no antibiotics were prescribed. The pathogenic condition cleared within 2 weeks, and significantly there was no further recurrence of abscess formation.

Cosmetic removal of moles and warts, were followed by application of a colophony preparation. Healing was rapid and without residual scarring.

A young adult male had a severe 2nd degree burn on his forearm with a massive effusion of plasma. Cotton and gauze bandages were applied and saturated with 35 weight percent colophony solution in olive oil. Within 48 hours the swelling began to subside, and within a week most of the effusion had disappeared. After a period of about 1 month, there was evidence of new epithelium formation. The burn injury healed without tissue scarring. The reduction of plasma effusion after severe burns is more rapid with the present invention chemotherapeutic compositions than is achieved with any other known burn therapy methods.

In an industrial accident, an adult male fell into a vat of boiling sodium hydroxide solution. He suffered trauma including 3rd degree burns on over 90 percent of the body skin surface area. The patient was placed in an oxygen tent and sedated with morphine and atropine. The patient was wrapped with thick cotton gauze bandages saturated with 35 weight percent rosin-olive oil solution. The saturated dressings were changed every 48 hours for the first 2 weeks, and thereafter every 96 hours. The patient was fed liquid nourishment orally, and maintained in the oxygen tent for 2 weeks. The regimen was continued for 2 months. After a period of 4 months the patient was able to walk and convalesce. The severe burn injuries had healed without scar formation. The patient resumed his employment a year after the occurrence of the accident.

An adult female suffered from a severe diabetic ulcer condition in the area of the right ankle. The patient was administered antibiotics and the ulcer was dressed with Dakin's solution. The ulcer increased in size, and the walls and base of the ulcer became necrotic. An arteriogram of the femoral artery revealed a closed dorsalis pedis artery. Treatment with a keratolytic enzyme appeared to worsen the condition. Gangrene developed, and amputation of the lower leg extremity was indicated. The case was referred for a regimen of treatment with 50 weight percent colophony-olive oil formulation. The entire right leg of the patient was placed in a boot with dressings saturated with the colophony formulation. The dressings were changed daily, and gradually the necrotic tissue peeled away. New blood vessels appeared in the center of the gangrenous area, and generation of granulation tissue was evident. After 6 weeks of treatment, the gangrenous tissue was replaced by healthy new tissue, and the patient made a full recovery without the need for amputation.

It is apparent that unique pharmacology is manifest in the many therapeutic benefits derived by treating skin disorders with colophony formulations. It has been observed that colophony formulations provide topical anesthetic relief, and inhibit infection of wound areas even without the use of antibiotics. In the case of ulcers and gangrene, the affected areas respond to colophony treatment, and there appears to be promotion of granulation tissue and stimulation of blood flow into the pathogenic tissue.

While not wishing to be bound by any theory or mechanism of reaction, it is believed that oleoresinous acids, such as abietic acid, penetrate the epidermis and underlying tissue and have a vascular chemotherapeutic effect. The exchange of arterial and venous fluid is stimulated, and the flow of fresh blood into damaged skin tissue is enhanced. The inhibition of infection by abietic acid and other resin acids present in colophony is perhaps attributable to stimulated activity of leukocytes and other natural anti-infection defenses.

Out of the earlier clinical investigations, there has evolved a group of new and preferred formulations which are adapted to be applied in the treatment of specific skin disorders with improved chemotherapeutic results.

It is a particularly preferred aspect of this invention to include $\alpha$-tocopherol as an essential component of the formulations. The effect of $\alpha$-tocopherol is to speed the healing process, and promote healing of skin injury without scarring.

The inclusion of other components in the formulations is advantageous for certain specific types of skin disorders. For example, for burn treatment a formulation can include between about 10 and 15 weight percent of anhydrous lanolin and/or between about 0.1 and 5 weight percent of boric acid based on formulation weight.

Experience with the present invention type formulations, would indicate that the inclusion of an antibiotic into the formulations should be avoided whenever possible. There is opinion that antibiotics adversely affect enzymatic activity, and interfere with homostasis of renal cells.

If it is required to include an antibiotic in the formulations, those that are effective against pseudomonas are highly preferred. Gentamicin and mafenide are mild drugs which are particularly suitable for burn treatment formulations. Silver sulfadiazine is also recommended for burn therapy.

In the case of serious infections such as in lymphangitis or phlebitis, a broad spectrum antibiotic can be incorporated into the formulation in a therapeutically effective quantity. Preferred antibiotics include achromycin, erthromycin, terramycin, vibramycin, chloroamphenicol, puromycin and cycloheximide.

The invention also contemplates the inclusion in the formulations of ingredients which enhance penetration of the skin by pharmacologically active substances. Solvents related to dialkylsulfoxides are examples of such ingredients (see U.S. Pat. No. 3,839,566). Preferred penetrants are higher ($C_8$-$C_{12}$) aliphatic sulfoxides such as octyl methyl sulfoxide, 2-hydroxydecyl methyl sulfoxide, and the like.

Abietic acid in the form of colophony or rosin may have a tendency to darken on standing. A pharmaceutically acceptable antioxidant can be included in the invention formulations for long term storage of the formulations, e.g., hydroquinone.

An important objective of the present invention is the provision of a medical regimen for the treatment of 2nd and 3rd degree burns, and burns which cover more than 30 percent of an individual body surface area, and particularly cases where the burns cover over 60 percent of the body area.

In the case of a severe burn syndrome, the following medical regimen is recommended. The patient is daily immersed in a bath of a solution of 50 weight percent abietic acid in olive oil for a period of time up to about 15 minutes. Where equipment is available, the patient is placed on a plastic covered surface in a hyperbaric chamber. The body is swathed in loose dressing saturated with a formulation of 25–35 weight percent abietic acid and a therapeutically effective quantity of $\alpha$-tocopherol dissolved in olive oil. The dressings are saturated every 24 to 96 hours, and changed as required. No antibiotic is included unless there is evidence of bacterial infection. The patient is fed liquids and nutrients. Mild sedation with librium or valium is advantageous. As soon as practical, passive motion in the patient is encouraged to prevent ankylosis. Early locomotion appears to be beneficial in minimizing keloid formation.

The following examples are illustrative of the preparation of chemotherapeutic formulations of the present invention. As it is apparent to those skilled in the art, in light of the foregoing disclosure, numerous modifications are possible in the practice of this invention without departing from the scope or concept thereof.

EXAMPLE 1

Formulation I suitable for treatment of 3rd degree burns is prepared as a homogeneous solution by admixture of the following ingredients:

| | |
|---|---|
| Abietic acid components of colophony | 450 grams |
| $\alpha$-Tocopherol | 100 grams |
| Olive oil | 1000 grams |

EXAMPLE 2

Formulation II suitable for treatment of burns complicated by pseudomonas infection is prepared from the following ingredients:

| | |
|---|---|
| Abietic acid (as colophony) | 308 grams |
| $\alpha$-Tocopherol | 100 grams |
| Gentamicin, 0.1% ointment | 20 grams |
| Olive oil | 1000 grams |

EXAMPLE 3

Formulation III suitable for treatment of burns is prepared from the following ingredients:

| | |
|---|---|
| Abietic acid anhydride and other components of colophony | 200 grams |
| $\alpha$-Tocopherol | 100 grams |
| Cod liver oil | 100 grams |
| Olive oil | 1000 grams |

The cod liver oil provides Vitamin A and Vitamin D in the formulation.

EXAMPLE 4

Formulation IV suitable for the treatment of burns is prepared from the following ingredients:

| | |
|---|---|
| Colophony | 664 grams |
| α-Tocopherol | 50 grams |
| Silver sulfadiazine | 10 grams |
| Cod liver oil | 50 grams |
| Olive oil | 1000 grams |

Boric acid unquentum can be included in the formulation in place of the cod liver oil.

EXAMPLE 5

Formulation V, recommended for treatment of small abscesses, and local infections of terminal phalanges of lower or upper extremities, comprises:

| | |
|---|---|
| Colophony | 315 grams |
| α-Tocopherol | 50 grams |
| Cod liver oil | 50 grams |
| Olive oil | 1000 grams |

EXAMPLE 6

Formulation VI suitable for treatment of large abscesses and lymph-angitis is prepared from the following ingredients:

| | |
|---|---|
| Colophony | 450 grams |
| Vitamin E | 50 grams |
| Gentamicin, 0.1% ointment | 115 grams |
| Cod liver oil | 50 grams |
| Olive oil | 1000 grams |

EXAMPLE 7

Formulation VII suitable for treatment of cellulitis and phlebitis is prepared from the following ingredients:

| | |
|---|---|
| Abietic acid | 581 grams |
| α-Tocopherol | 50 grams |
| Mafenide 8.5% ointment | 20 grams |
| Cod liver oil | 50 grams |
| Olive oil | 1000 grams |

For treatment of abrasions and puncture wounds, vaseline can be substituted for the cod liver oil and/or the olive oil.

For improved penetration of the traumatized area, between about 0.1 and 10 weight percent, based on formulation weight, of octyl methyl sulfoxide or other penetrant can be incorporated in the formulation.

EXAMPLE 8

Formulation VIII, recommended for the treatment of decubitus ulcers, comprises:

| | |
|---|---|
| Abietic acid anhydride (e.g., rosin) | 417 grams |
| Vitamin E | 100 grams |
| Gentamicin, 0.1% ointment | 15 grams |
| Cod liver oil | 100 grams |
| Cottonseed oil | 1000 grams |

EXAMPLE 9

Formulation IX suitable for treatment of diabetic ulcers and impending gangrene is prepared from the following ingredients:

| | |
|---|---|
| Colophony | 638 grams |
| α-Tocopherol | 100 grams |
| Cod liver oil | 50 grams |
| Olive oil | 1000 grams |
| Decyl methyl sulfoxide (optional) | 50 grams |

EXAMPLE 10

Formulation X, recommended for treatment of varicose, traumatic, indolent and arteriosclerotic ulcers, comprises:

| | |
|---|---|
| Abietic acid | 418 grams |
| α-Tocopherol | 50 grams |
| Gentamicin, 0.1% ointment | 15 grams |
| Cod liver oil | 50 grams |
| Lanolin, anhydrous | 50 grams |
| Olive oil | 1000 grams |

EXAMPLE 11

Formulation XI, suitable as an adjunct in plastic and reconstruction surgery is prepared from ingredients comprising:

| | |
|---|---|
| Abietic acid | 225 grams |
| α-Tocopherol | 100 grams |
| Olive oil | 1000 grams |

EXAMPLE 12

Formulation XII, suitable for use in plastic and reconstruction surgery is prepared from the following ingredients:

| | |
|---|---|
| Colophony | 400 grams |
| Vitamin E mixed tocopherol | 100 grams |
| Cod liver oil | 100 grams |
| Olive oil | 1000 grams |

EXAMPLE 13

Formulation XIII, recommended for use in plastic and reconstruction surgery, comprises:

| | |
|---|---|
| Colophony | 546 grams |
| α-Tocopherol | 100 grams |
| Gentamicin, 0.1% ointment | 20 grams |
| Lanolin, anhydrous | 100 grams |
| Olive oil | 1000 grams |

EXAMPLE 14

Formulation XIV, recommended for use in skin graft surgery, comprises:

| | |
|---|---|
| Colophony | 450 grams |
| α-Tocopherol | 50 grams |
| Cod liver oil | 50 grams |
| Olive oil | 1000 grams |

In one method, the denuded area of the skin graft site is covered with a basket weave of plastic or adhesive strips and topped with a dressing saturated with Formulation XIV.

What is claimed is:

1. A method for treating second and third degree burns covering more than 30 percent of the skin surface of an animal or human body which comprises applying to the burned skin surface a pharmaceutical preparation comprising between about 25 and 60 weight percent colophony dissolved in a pharmaceutically acceptable vegetable oil.

2. A method of treatment in accordance with claim 1 wherein the burns cover more than 60 percent of the skin surface of the body.

3. A method for treating second and third degree burns covering more than 30 percent of the skin surface of an animal or human body which comprises applying to the burned skin surface a pharmaceutical preparation comprising between about 25 and 60 weight percent colophony dissolved in a pharmaceutically acceptable fish oil.

4. A method of treatment in accordance with claim 3 wherein the burns cover more than 60 percent of the skin surface of the body.

5. A method for treating second and third degree burns covering more than 30 percent of the skin surface of an animal or human body which comprises applying to the burned skin surface a pharmaceutical preparation comprising between about 25 and 60 weight percent colophony dissolved in lanolin.

6. A method of treatment in accordance with claim 5 wherein the burns cover more than 60 percent of the skin surface of the body.

* * * * *